US00PP09484P

United States Patent [19]

Magee

[11] Patent Number: Plant 9,484

[45] Date of Patent: Mar. 26, 1996

[54] ILEX HYBRID VARIETY NAMED 'CONED'

[75] Inventor: Jack M. Magee, Hwy. 26 W. Rte. 1 Box 297, Poplarville, Miss. 39470

[73] Assignees: Jack Mitchell Magee, Poplarville, Miss.; Flowerwood Nsy Inc., Mobile, Ala.

[21] Appl. No.: 400,031

[22] Filed: Mar. 6, 1995

[51] Int. Cl.[6] ..... A01H 5/00

[52] U.S. Cl. ..... Plt./65

[58] Field of Search ..... Plt./65

[56] References Cited

U.S. PATENT DOCUMENTS

P.P. 8,792 6/1994 Fischer ..... Plt./65

P.P. 8,793 6/1994 Fischer ..... Plt./65

*Primary Examiner*—James R. Feyrer

[57] ABSTRACT

A new and distinct variety of Ilex plant found as a openly pollinated seedling of Ilex Hybrid 'Mary Nell'. The new variety expresses a very high concentration of anthocyanin in new growth which matures to a lustrous green color. This plant is superior in development of an upright, dense, globose shaped canopy with attractive spiny leaves and orange-red fruit.

2 Drawing Sheets

BACKGROUND OF THE INVENTION

This new Ilex variety was found as an openly pollinated seedling of Ilex Hybrid 'Mary Nell', an unpatented variety, maintained in the Evergreen Nursery at Poplarville, Miss. The seedling was found in May, 1989. The new and distinct Ilex Hybrid plant of this invention comprises a novel and valuable holly plant with an upright, dense, rounded shape and attractive reddish-purple new growth. The new growth of this plant is interestingly and clearly red due to anthocyanin, which is of distinctly higher concentration than in the parent variety. As with the parent plant, the plant of this invention may be advantageously employed as a specimen appointment, in either formal or informal groupings, and is very attractive in mass plantings. The plant serves well in foundation plantings and is adapted for culture as a potted plant. This plant is responsive to pruning and training and may be used in forming dense, attractive hedges, and maintained without an excessive amount of care. This plant is easy to care for and maintain in size due to its smaller stature, heavy branching, and dense canopy.

Asexual propagation of the new plant by cutting has been under Mr. Magee's direction at the same location. Several generations of the new plant have been evaluated and the distinctive characteristics of the plant have remained stable.

SUMMARY OF THE INVENTION

The following are the most outstanding and distinguishing characteristics of this new cultivar when grown under normal horticultural practices in Poplarville, Miss.

1. Upright, dense, and globose in nature.
2. The Reddish/Purple color of the new foliage is unique and offers a novel and strikingly appealing contrast of new foliage to old foliage in plants of this market class.
3. Hardy to Zone 7
4. Heat and drought tolerant.
5. Fast growth rate under normal fertilization and moisture conditions.
6. Tolerates most soils from moist to dry and from sand to clay.

7. Relatively pest resistant.
8. Very desirable in planters.
9. Makes a good hedge.
10. Easy to root from cuttings collected anytime of year.
11. Produces attractive orange-red fruit in the fall which persist into the winter and may result in bird visitation.
12. Has the ability to be sheared and trimmed to be kept within prescribed limits.
13. Mature leaves are a rich lustrous green color with attractive spines.

DESCRIPTION OF THE DRAWINGS

This new Ilex Hybrid variety is illustrated by the accompanying photographic prints in which.

Figure 1:
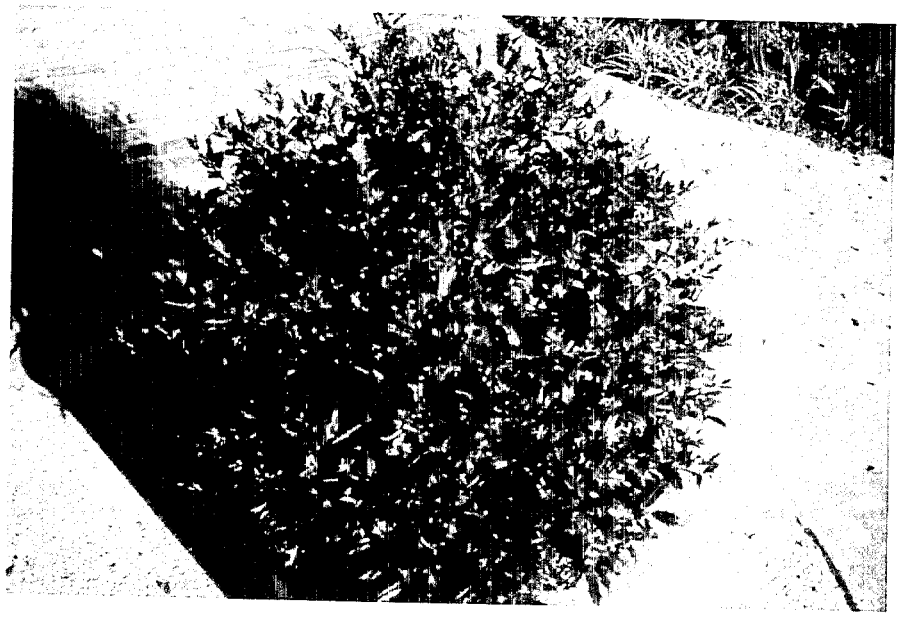
FIG. 1 discloses the dense rounded shape and the reddish-purple new growth of the new variety.
Figure 2:
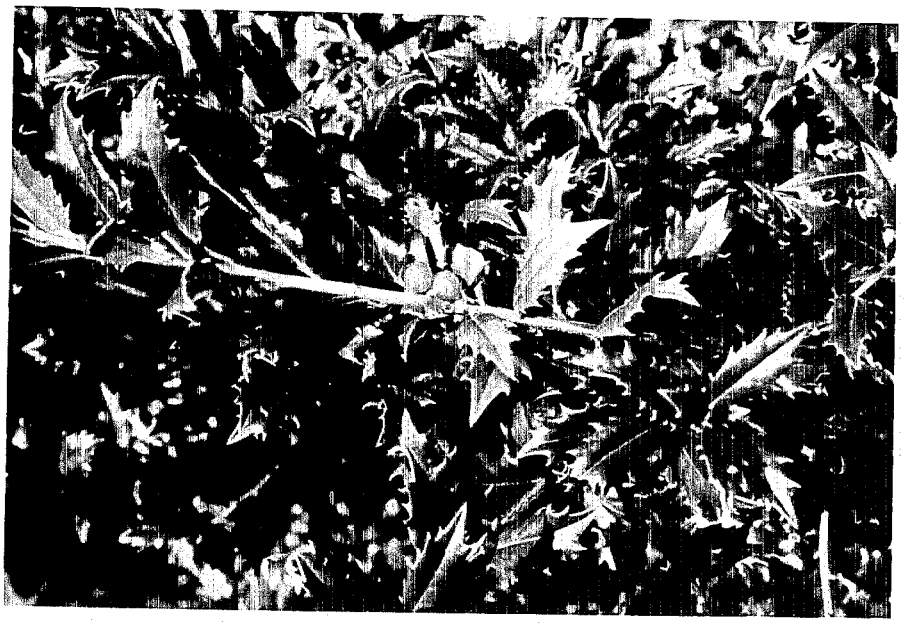
FIG. 2 shows a close-up view of the attractive orange-red fruit and mature foliage of the new variety.
Figure 3:
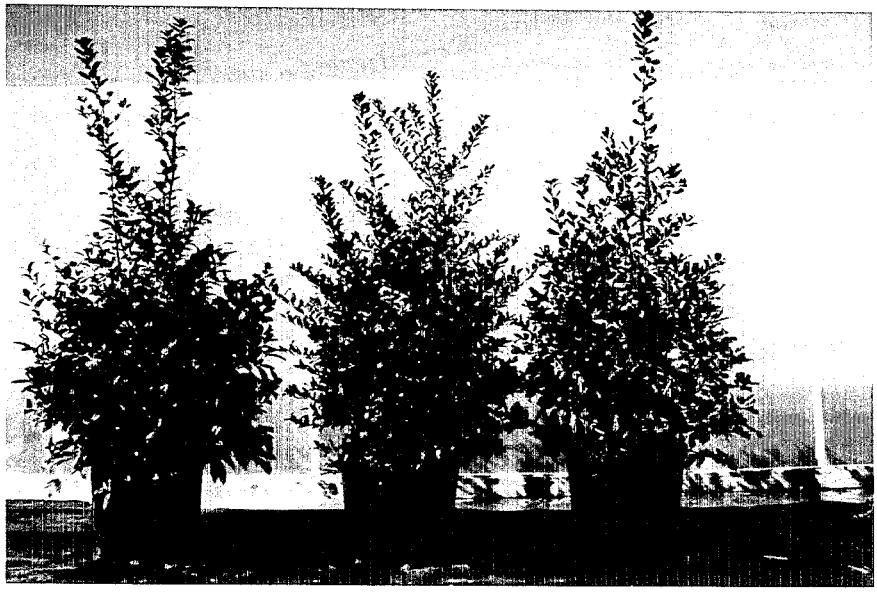
FIG. 3 is a side-by-side photograph of (from left to right) the parent plant Ilex Hybrid 'Mary Nell', the new variety, and Ilex Hybrid 'Nellie R. Stevens'. The mid-winter photograph shows the new variety's upright, dense, rounded shape and slightly lighter mature foliage color.
Figure 4:
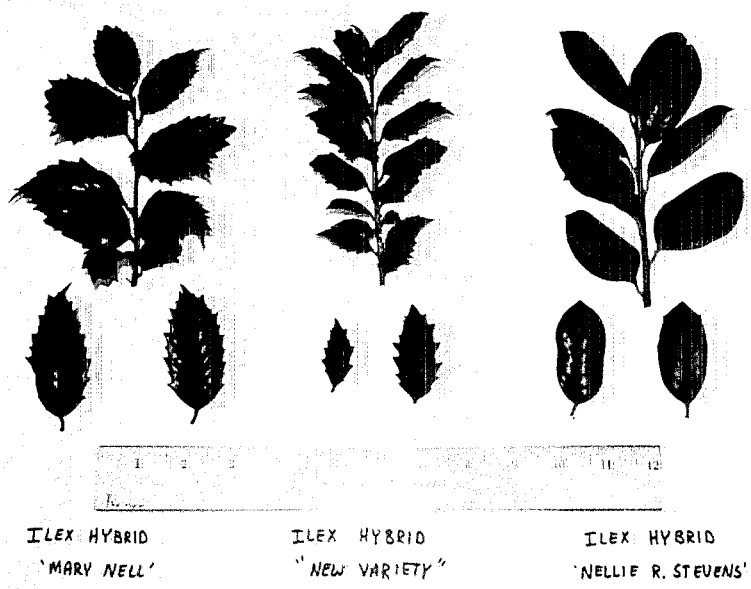
FIG. 4 is also a side-by-side photograph illustrating the leaf shapes and sizes of (from left to right) the parent plant Ilex Hybrid 'Mary Nell', the new variety, and Ilex Hybrid 'Nellie R. Stevens'. Also evident is the less glossy leaf of the new variety compared to the other hollies.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Ilex based on my observations made of plants grown in wholesale commercial production practices, in greenhouses, and established landscape plantings in Poplarville, Miss.

| | Distinctive Characteristics: | | |
|---|---|---|---|
| Characteristic | 'Coned' | 'Mary Nell' | 'Nellie R. Stevens' |
| Height (Mature) | 10–12' | 15–20' | 15–25' |
| Width (Mature) | 8–10' | 12–15' | 12–15' |
| Leaf Length | 2–2 ¾" | 2 ⅝–3 ½" | 2 ¼–3" |
| Leaf Width | ⅞–1 ¼" | 1 ⅛–1 ¾" | 1–1 ½" |
| Leaf Color (Immature) | Greyed-Purple Group 187A | Yellow-Green Group 144A | Yellow-Green Group 144A |
| Leaf Color (Mature) | Closest to Green Group 139A | Green Group 139A | Green Group 139A |
| Leaf Glossiness (Mature) | Lustrous | Very glossy | Glossy |
| Leaf Shape | Ovate to narrowly lanceolate | Ovate to broadly lanceolate | Ovate |
| Leaf Spines (Pairs) | 7–9 | 9–11 | 2–3 |
| Fruit Color | Orange-Red Group 33A | Red Group 40A | Orange-Red Group 33A |
| Flowers Sex | Female only | Female only | Female only |
| Leaf Base | Cuneate | Obtuse | Obtuse |
| Mature Shape | Upright Dense & Globose | Upright Pyramidal | Upright Pyramidal rounded with age |
| Hardiness | Zone 7 | Zone 7 | Zone 6 |

The parent plants of the new variety 'Coned' is Ilex 'Mary Nell' which originated from a controlled cross made in 1962 by Joe McDaniel at Tom Dodd Nurseries in Semmes, Ala. The female parent was *Ilex* (*cornuta 'Burfordii'×pernyi*) 'Red Delight', A selection of Henry Hohman, Kingsville Nurseries, Kingsville, Md. The male parent was *Ilex latifolia.* Ilex 'Mary Nell' was named in 1981 by Thomas H. Dodd., Jr. after Joe McDaniel's wife.

Ilex Hybrid 'Nellie R. Stevens'. which is very popular in the industry, is a hybrid between *Ilex aquifolium* and *Ilex cornuta.* It was released by G. A. Van-Lennep, Jr., St. Michael, Md. in 1954. It is named for the owner, Nellie R. Stevens, Oxford, Md. This non-patented plant is comparable to the new plant, however, there are many differences. The immature foliage of the new variety is Greyed-Purple Group 187A compared to Yellow-Green Group 144A of Ilex 'Nellie R. Stevens'. The new variety also has more spines, 7–9 (pairs) compared to 2–3 (pairs), less glossy mature leaves, and has a smaller overall plant size.

It is from the openly pollinated seedlings of the Ilex 'Mary Nell' plant that I found the new plant. This new variety will be sold under the trademark Little Red.

Classification:

*Botanic.*—Ilex Hybrid 'Coned'.

Form: Upright, dense, and rounded.

Texture: Medium.

Height: 10–12'.

Width: 8–10'.

Growth habit: Upright, dense, and globose. Fast growth rate under normal fertilization and moisture conditions.

Foliage: Alternate, simple, evergreen, ovate to narrowly lanceolate, and vary in size from 2–2 ¾" long and ⅞–1 ¼" wide. The margins are slightly recurved and serrate with 7–9 pairs of prominent spines. The spines vary in length and width from 1/16 to 3/16" and usually alternate between long and short. The apex is acute and has a single spine and the base is cuneate. The petiole is ¼–⅜" long. Mid-veins and laterals are impressed on the upper leaf surface and the mid-veins are prominent on the underside. The upper surface of the immature leaves are glossy, glabrous, and are Grey-Purple Group 187A. The lower surface of the immature leaves are Grey-Purple Group 186B and matte. As the leaves mature they become less glossy and the upper surfaces becomes closest to Green Group 139A and the lower leaf surface becomes Yellow-Green Group 146C. This mature leaf color persists through the winter. Although the mature leaf color of the new variety is closest to Green Group 139A, which is also the color of the parent plant, it appears to be a shade lighter when viewed in full sun. This could be due in part to the less glossy leaf surface of the new variety.

In 1992, the date of initial spring growth was March 10, in Poplarville, Miss. After the initial spring flush there was almost continuous growth until fall ending October 22, also in Poplarville, Miss. This growth pattern was identical to the parent plant. When grown in full sun, the internode length of this plant is ½–¾" compared to ⅝–1¼" for the parent plant. When grown in light shade the internode length is ¾–1". As would be expected either plant grown in the shade results in a taller less dense plant with larger leaves.

The average length of terminal growth of the initial spring flush is about 10" for a plant in full sun and 12" when grown in shade. After this initial flush we normally trim the plant lightly and the plant then continue to grow about 6" until we trim it a second time in the early fall. The fall growth of about 8" then hides the cut limbs. We finish in the fall with a three gallon plant about 28" tall and 24" wide. I have not noticed a difference in vigor between this plant and the parent, however, its shorter internode length and increased branching results in a shorter more dense plant. Ilex 'Mary Nell' plants grown under identical conditions were 34" tall and 20" wide at the end of the fall. Although there are many variable involved it shoud take about 8–10 years for this plant to reach a mature height of 10–12' tall and width 8–10'. In the landscape little or no pruning is necessary to produce a dense and rounded shrub in full sun. In shade, however, some trimming may be needed to produce the same effect.

Stems: The young shoots and petioles have a pronounced purple pigmentation, Greyed-Purple Group 187A, and are matte. As the stems mature they become Yellow-Green Group 144A. The stem tips (½–1") and petioles retain the purple pigmentation into the winter. After one or more years the stems are generally Green-Brown Group 199C, glabrous and rugose. The pith is solid and uniform. Young and older stems are densely branched.

Flowers: Small, creamy yellow, inconspicuous, slightly fragrant, borne on previous season's growth from March to May. Flower structure of this plant is identical to that of the parent plant. Buds are globular, Yellow-Green Group 144A, and without foliaceous appendages. Flowers are clustered in the leaf axils and are 4-merous. Unbranched pedicels are about ¼" long and Yellow-Green Group 144A. The four ovate petals are arranged regularly, united at the base, and imbricate in bud. The ovary protrudes from the receptacle and is Green Group 143A. There are four stamen with underdeveloped anthers which are White Group 155D. No pollen is produced. Blooms are small to medium in size, Yellow Group 2D, ⅜" diameter, and last on the plant in the garden 2–4 days.

Fruit: Drupaceous, globose, ¼–⅜" diameter, borne fasciculate with 2–5 fruits on short unbranched pedicels ¼" long. Each fruit contains 4 pyrenes. Matures to Orange-Red Group 33A in mid - Nov. in Poplarville, Miss. and persists into the winter. Normally fruit set is not heavy.

Culture: Grows well in a wide range of conditions and tolerates sun to part shade. Grows in nearly any soil type, from moist to very dry and sand to clay. Responds well to mulching and medium applications of fertilizer; prefers ph 5 to 6.5. Little pruning is needed. Can be sheared. Propagated with semi-hardwood cutting anytime of the year.

Pests: None serious.

I claim:

1. A new and unique variety of Ilex plant named Ilex Hybrid 'Coned' as herein shown and described, is characterized by its upright, dense, and globose growth habit, unique juvenile foliage coloration, lustrous mature leaves, distinctly arranged leaf serrations, orange-red fruit, fast growth rate, resistance to pests, and tolerance of heat, drought, and soil type.

* * * * *